US011052025B2

(12) United States Patent
Boucenna Verdier et al.

(10) Patent No.: US 11,052,025 B2
(45) Date of Patent: Jul. 6, 2021

(54) PERFUMES IN THE FORM OF AQUEOUS MICROEMULSIONS

(71) Applicants: CHANEL PARFUMS BEAUTE, Neuilly sur Seine (FR); UNIVERSITE SCIENCES TECHNOLOGIES LILLE, Villeneuve d'Ascq (FR)

(72) Inventors: Oriana Boucenna Verdier, Les Pavillons Sous Bois (FR); Christian Mahe, Neuilly sur Seine (FR); Véronique Rataj-Nardello, Pont a Marcq (FR); Jean-Marie Aubry, Oignies (FR); Maxime Nollet, Lyons (FR); Raphaël Lebeuf, Lille (FR)

(73) Assignees: CHANEL PARFUMS BEAUTE, Neuilly sur Seine (FR); UNIVERSITE DE LILLE, Lille (FR)

( * ) Notice: Subject to any disclaimer, the term of this patent is extended or adjusted under 35 U.S.C. 154(b) by 309 days.

(21) Appl. No.: 16/304,773

(22) PCT Filed: Jun. 1, 2017

(86) PCT No.: PCT/FR2017/051373
§ 371 (c)(1),
(2) Date: Nov. 27, 2018

(87) PCT Pub. No.: WO2017/207935
PCT Pub. Date: Dec. 7, 2017

(65) Prior Publication Data
US 2020/0323749 A1   Oct. 15, 2020

(30) Foreign Application Priority Data

Jun. 1, 2016   (FR) .................................... 16 54983

(51) Int. Cl.
| | | |
|---|---|---|
| *A61Q 13/00* | (2006.01) | |
| *A61K 8/06* | (2006.01) | |
| *A61K 8/33* | (2006.01) | |
| *A61K 8/34* | (2006.01) | |
| *A61K 8/35* | (2006.01) | |
| *A61K 8/37* | (2006.01) | |
| *A61K 8/44* | (2006.01) | |
| *A61K 8/46* | (2006.01) | |
| *A61K 8/49* | (2006.01) | |
| *A61K 8/60* | (2006.01) | |

(52) U.S. Cl.
CPC .............. *A61K 8/068* (2013.01); *A61K 8/062* (2013.01); *A61K 8/33* (2013.01); *A61K 8/34* (2013.01); *A61K 8/342* (2013.01); *A61K 8/35* (2013.01); *A61K 8/37* (2013.01); *A61K 8/442* (2013.01); *A61K 8/463* (2013.01); *A61K 8/466* (2013.01); *A61K 8/4973* (2013.01); *A61K 8/602* (2013.01); *A61Q 13/00* (2013.01); *A61K 2800/30* (2013.01); *A61K 2800/596* (2013.01)

(58) Field of Classification Search
CPC . A61Q 13/00; A61K 8/37; A61K 8/34; A61K 8/35; A61K 8/33; A61K 8/4973; A61K 8/342; A61K 2800/10; A61K 8/463; A61K 8/068; A61K 8/466; A61K 8/602; A61K 2800/596; A61K 8/442; A61K 8/064
USPC ......................................................... 424/401
See application file for complete search history.

(56) References Cited

U.S. PATENT DOCUMENTS

2009/0130029 A1   5/2009   Tamarkin et al.
2012/0097754 A1*  4/2012   Vlad ......................... A61L 9/01
                                                     239/6

FOREIGN PATENT DOCUMENTS

FR        2998476 A1      5/2014
WO   WO 2014080150 A1 *  5/2014 ............. A61Q 13/00

OTHER PUBLICATIONS

STIC Search Report dated Dec. 31, 2020.*
International Search Report, dated Sep. 8, 2017, from corresponding PCT application No. PCT/FR2017/051373.
García, José I., et al. "Green solvents from glycerol. Synthesis and physico-chemical properties of alkyl glycerol ethers." Green Chemistry 12.3 (2010): 426-434.

* cited by examiner

*Primary Examiner* — Eisa B Elhilo
(74) *Attorney, Agent, or Firm* — Nixon & Vanderhye

(57) ABSTRACT

Disclosed is a microemulsion of oil-in-water type including, preferably consisting of, by weight relative to the total weight of microemulsion: •70% to 94% of water, •1% to 15% of at least one hydrophobic fragrancing substance, •4% to 20% of at least one preferably volatile solvo-surfactant, and •0.1% to 15%, preferably 1% to 13%, of at least one hydrotropic agent or at least one surfactant selected from anionic surfactants, cationic surfactants, amphoteric surfactants and non-ionic surfactants. The solvo-surfactant is selected from monoalkylated glycerol derivatives of following formula (I):

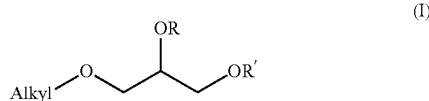

wherein the "alkyl" group is a linear or branched alkyl group including from 1 to 8 carbon atoms, and R and R' are each independently H or a linear or branched alkyl group including from 1 to 5 carbon atoms, with the proviso that R is different from R', and mixtures thereof.

13 Claims, No Drawings

PERFUMES IN THE FORM OF AQUEOUS MICROEMULSIONS

The invention relates to aqueous volatile fragrancing microemulsions based on the use of solvo-surfactants.

Perfumes conventionally comprise alcohols such as ethanol or else isopropanol as solvents. However, the use of these solvents has a certain number of disadvantages: they are highly volatile and inflammable, leading to a certain amount of danger when producing them, and to a certain extent when using them. Their own odor may also interfere with that of the perfume. In addition, applied to the skin or the hair, these perfumes may lead to drying out, in particular in consumers with sensitive skin.

Therefore, there is currently an emergence of new compositions, especially for reasons of public health and/or ecology. The goal being pursued is that of decreasing or even eliminating volatile organic compounds (such as alcohols) contained in perfumes, by developing fragrancing compositions in the form of stable aqueous dispersions or solutions.

However, the majority of fragrancing molecules are hydrophobic and are therefore not water-soluble. In order to overcome this problem, use must be made of surfactants that make it possible to dissolve fragrancing molecules within micelles, forming microemulsions. It is desirable that the swollen micelles containing the fragrances are small so that the fragrancing composition has a transparent, or at the very least translucent, appearance. Thus, the production of microemulsions meeting this criterion of transparent appearance is of particular benefit.

Other constraints are linked to the thermodynamic stability of the microemulsion, to the non-tacky nature thereof, and to the absence of residue on the skin or on the clothes. It is therefore important to be able to prepare them using as little surfactant as possible.

There is therefore a need for a stable fragrancing composition containing a large amount of fragrance, which is transparent or at least translucent, and which contains as little surfactant as possible.

The aim of the present invention is to provide aqueous, transparent microemulsions that are substantially free of ethanol, containing at least one hydrophobic fragrancing substance (preferably at least 3% and preferentially approximately 10% of fragrance) and at least one volatile solvo-surfactant. Such odoriferous or fragrancing microemulsions are stable and comprises as little as possible of substances that cause undesirable effects, in particular to the skin and/or the environment.

According to the invention, a substance is "volatile" when its boiling point is less than 250° C. at atmospheric pressure. The "non-volatile" compounds have a boiling point of greater than 250° C. at atmospheric pressure.

The present invention therefore relates to a microemulsion of oil-in-water type comprising, preferably consisting of, by weight relative to the total weight of microemulsion:
- 70% to 94% of water,
- 1% to 15% of at least one hydrophobic fragrancing substance,
- 4% to 20% of at least one preferably volatile solvo-surfactant, and
- 0.1% to 15%, preferably 1% to 13%, of at least one hydrotropic agent or at least one surfactant selected from anionic surfactants, cationic surfactants, amphoteric surfactants and non-ionic surfactants, said solvo-surfactant being selected from an isosorbide compound obtained in the following 2 endo and exo forms:

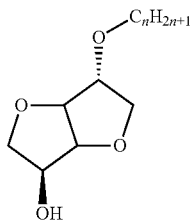 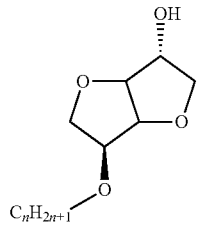

wherein n = 3, the monoalkylated glycerol derivatives of following formula (I):

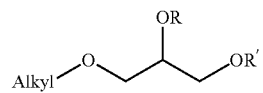

wherein the "alkyl" group is a linear or branched alkyl group comprising from 1 to 8 carbon atoms, and R and R' are each independently H or a linear or branched alkyl group comprising from 1 to 5 carbon atoms, preferably a methyl or ethyl group, with the proviso that R is different from R', and mixtures thereof.

The present invention therefore relates to a microemulsion of oil-in-water type comprising, preferably consisting of, by weight relative to the total weight of microemulsion:
- 70% to 94% of water,
- 1% to 15% of at least one hydrophobic fragrancing substance,
- 4% to 20% of at least one preferably volatile solvo-surfactant, and
- 0.1% to 15%, preferably 1% to 13%, of at least one hydrotropic agent or at least one surfactant selected from anionic surfactants, cationic surfactants, amphoteric surfactants and non-ionic surfactants, said solvo-surfactant being selected from the mixtures of
i) an isosorbide compound obtained in the following 2 endo and exo forms:

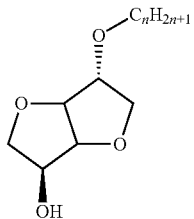 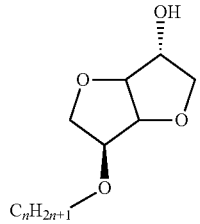

wherein n = 4 or 5, and ii) a monoalkylated glycerol derivative of following formula (I):

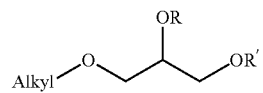

wherein the "alkyl" group is a linear or branched alkyl group comprising from 1 to 8 carbon atoms, and R and R' are each independently H or a linear or branched alkyl group comprising from 1 to 5 carbon atoms, preferably a methyl or ethyl group, with the proviso that R is different from R'.

The microemulsion according to the invention optionally comprises from 0.01% to 2% by weight of at least one preservative.

The microemulsion according to the invention is preferably substantially free of ethanol, i.e. it comprises less than 3% by weight of ethanol, preferably less than 2% by weight of ethanol, preferably less than 1% by weight of ethanol. More preferentially, it is devoid of ethanol, i.e. it contains 0% by weight of ethanol.

The monoalkylated glycerol derivatives are preferably the derivatives of following formula (I):

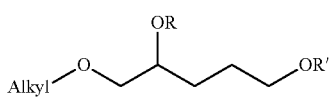

(I)

wherein the "alkyl" group is a linear or branched alkyl group comprising from 1 to 6 carbon atoms, and R and R' are each independently H or a linear or branched alkyl group comprising from 1 to 5 carbon atoms, preferably a methyl or ethyl group, with the proviso that R is different from R'.

The monoalkylated glycerol derivatives are preferably the derivatives of following formula (I):

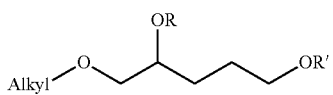

(I)

wherein the "alkyl" group is a linear or branched alkyl group comprising 3, 4 or 5 carbon atoms, and R and R' are each independently H or a linear or branched alkyl comprising from 1 to 5 carbon atoms, preferably a methyl or ethyl group, with the proviso that R is different from R'. The monoalkylated glycerol derivatives are more preferentially the derivatives of following formula (I):

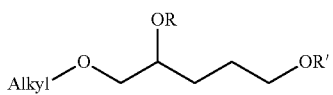

(I)

wherein the "alkyl" group is a linear or branched alkyl group comprising 3, 4 or 5 carbon atoms, R is a methyl group and R' is H.

"Microemulsion of oil-in-water type" denotes a liquid system in which an oily (or hydrophobic) phase is dispersed in a continuous aqueous (or hydrophilic) phase so as to form drops of a diameter of less than 100 nm. The oil/water interface is stabilized by surfactant compounds. The drops preferably have a diameter of between 2 and 100 nm.

These microemulsions have drops which are invisible to the naked eye and to optical microscopes. They are transparent, or at the very least translucent, unlike emulsions, which is a desired property especially for fragrancing compositions.

"Hydrophobic substance" denotes a pure substance or a mixture that is water-insoluble or only very sparingly water-soluble by nature. A possible method to determine the hydrophobicity of substances is to measure their solubility in different solvents, or the retention time on a chromatographic column (by high-performance liquid chromatography, HPLC) of said hydrophobic substance.

The hydrophobic substances according to the invention are fragrancing, i.e. they are odoriferous and may be used in perfumes. "Odoriferous substance" is intended to mean a substance that can be olfactorily detected by a subject and/or by olfactometry, according to principles known to those skilled in the art. An example of a method making it possible to detect an odoriferous substance is described in document EP 0003088. Other techniques for detecting an odoriferous substance are applicable, such as gas chromatography techniques, mass spectroscopy techniques or else infrared absorption analysis techniques. Odoriferous substance is also intended to mean a substance which gives off an odor, preferably an odor that is pleasant for at least 20% of people, in particular a fragrance.

The hydrophobic fragrancing substance is preferably a natural or synthetic hydrophobic fragrancing substance, more preferentially natural. It is more preferentially selected from terpenes, essential oils and natural compounds having odoriferous properties (terpenoids), especially selected from aldehydes, esters, ketones, alcohols, phenols, alkenes and ethers.

"Terpenes" denotes hydrocarbons in which the base component is isoprene, their empirical formula comprising a number of carbons that is a multiple of 5, in particular terpenes containing especially 10 or 15 carbon atoms, used in perfumery.

"Terpenoids" denotes terpene derivatives, for example alcohols, phenols, ketones, aldehydes, esters or ethers.

Terpenes and terpenoids are contained in "essential oils", denoting the concentrated liquid that is commonly odoriferous, volatile, and produced by plants. Essential oils are most commonly extracted from plant organs by hydrodistillation especially, but the constituents of these oils are widely industrially synthesized.

Use may especially be made of the following natural hydrophobic fragrancing substances:
 terpenes: pinenes, camphenes, limonene, cadinene, carene, caryophyllene,
 alcohols: linalool, geraniol, menthol, citronellol,
 ketones: menthone, carvone, beta-ionone, thujone, camphor, cyclopentadecanone,
 aldehydes: citral, citrannal, citronellal, cinnamic aldehyde, lilial,
 esters: linalyl acetate, menthyl acetate, geranyl acetate, geranyl succinate,
 phenols: thymol, carvacrol, eugenol, isoeugenol,
 ethers: anethole, eucalyptol, cineole, rose oxide,
 alkenes: limonene.

The essential oils may be oils of ylang-ylang, bergamot, *eucalyptus*, lavender, lavandin, lemongrass, patchouli, peppermint, pine, rose, coriander, Shiu, sage, geranium, palmarosa, *Litsea cubeba*, lemon, citronnella, orange blossom, grapefruit, lime, mandarin, tangerine, orange, cajeput, camphor, rosemary, green anise, star anise, fennel, basil, tarragon, clove, chilli, thyme, *sassafras*, wormwood, mugwort, cedar, hyssop, *tagetes*, rue, elemi, *galbanum*, juniper berries, cabreuva, lignum vitae, sandalwood, vetiver, ambrette, *angelica*, iris rhizome, carrot, celery, cumin, lovage, parsley, cinnamon, cardamom, ginger, nutmeg, pepper, frankincense, myrrh, Peru balsam, *styrax*, buchu, chamomile or rock rose (Jean Garnero, "Huiles essentielles" [Essential oils], Techniques de l'ingénieur, Traité constantes physico-chimiques, K-345). The amount of hydrophobic fragrancing substances in the microemulsions according to the invention is between 1% and 15% by weight, preferably between 5% and 12% by weight relative to the total weight of microemulsion.

"Solvo-surfactant" denotes an amphiphilic compound that brings together some properties of surfactants, especially reduction of water/air surface tension and oil/water interfacial tension, the ability to self-associate in water, and some properties of solvents, especially the ability to evaporate without leaving residues.

The solvo-surfactant is preferably volatile and is an isosorbide compound obtained in the following 2 endo and exo forms:

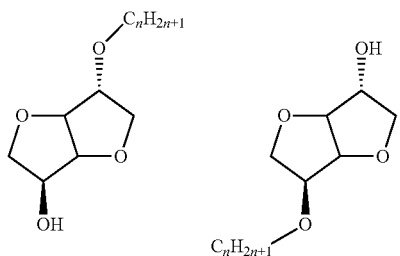

These two compounds are derivatives of isosorbide, in endo and exo form. The 35:65 mixture of these compounds is referred to as "C3Iso" in the examples of the present application. Stereoselectivity leads to this ratio of the endo/exo mixture being obtained.

Preferably, alternatively, the solvo-surfactant is volatile and is selected from monoalkylated glycerol derivatives of following formula (I):

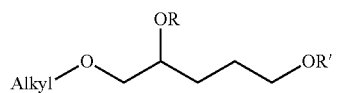

wherein the "alkyl" group is a linear or branched alkyl group comprising 1 to 8 carbon atoms, and R and R' are each independently H or a linear or branched alkyl group comprising from 1 to 5 carbon atoms, preferably a methyl or ethyl group, with the proviso that R is different from R'.

More preferentially, the solvo-surfactant is the monoalkylated glycerol derivative of formula (I), wherein the "alkyl" group is a linear alkyl group comprising 3, 4 or 5 carbon atoms, and R and R' are each independently H or a methyl or ethyl group, with the proviso that R is different from R'.

More preferentially, the solvo-surfactant is the monoalkylated glycerol derivative of formula (I), wherein the "alkyl" group is a linear alkyl group comprising 3, 4 or 5 carbon atoms, R is a methyl or ethyl group, and R' is H.

The monoalkylated glycerol derivative of formula (I) wherein the "alkyl" group is a linear alkyl group comprising 3 carbon atoms (propyl group), R is H and R' is methyl, is 1-methoxy-3-propoxypropan-2-ol. It is referred to as "C301" in the examples of the present application. The monoalkylated glycerol derivative of formula (I) wherein the "alkyl" group is a linear alkyl group comprising 3 carbon atoms (propyl group), R is methyl and R' is H, is 2-methoxy-3-propoxypropan-1-ol. It is referred to as "C310" in the examples of the present application.

The monoalkylated glycerol derivative of formula (I) wherein the "alkyl" group is a linear alkyl group comprising 4 carbon atoms (butyl group), R is H and R' is methyl, is 1-methoxy-3-butoxypropan-2-ol. It is referred to as "C401" in the examples of the present application. The monoalkylated glycerol derivative of formula (I) wherein the "alkyl" group is a linear alkyl group comprising 4 carbon atoms (butyl group), R is methyl and R' is H, is 2-methoxy-3-butoxypropan-1-ol. It is referred to as "C410" in the examples of the present application.

The monoalkylated glycerol derivative of formula (I) wherein the "alkyl" group is a linear alkyl group comprising 5 carbon atoms (pentyl group), R is H and R' is methyl, is 1-methoxy-3-pentoxypropan-2-ol. It is referred to as "C501" in the examples of the present application. The monoalkylated glycerol derivative of formula (I) wherein the "alkyl" group is a linear alkyl group comprising 5 carbon atoms (pentyl group), R is methyl and R' is H, is 2-methoxy-3-pentoxypropan-1-ol. It is referred to as "C510" in the examples of the present application.

The amount of volatile solvo-surfactant(s) in the microemulsion according to the invention is between 5% and 20% by weight, preferably between 7% and 18% by weight.

The microemulsions according to the invention have a fragrance quality that is stable over time, corresponding to the standard shelf life of a cosmetic product, and stable at temperatures from 5 to 45° C. or from 15 to 45° C., corresponding to the temperatures of exposure and use of a cosmetic product.

The technical criteria of the quality of a fragrance, in the case of an aqueous fragrance, are:
the ability of a fragranced composition to maintain, after application, an olfactory perception threshold over time,
the ability of a composition, once applied, to maintain its olfactory form over time,
the ability of a composition to not undergo endogenous or exogenous alterations that could modify its olfactory form, and
harmlessness, which is the ability of a composition to not produce undesirable effects once it is applied to the skin of the user.

"Hydrotropic agent" is intended to mean an amphiphilic compound comprising hydrophilic functional groups, used to enable the solubilization of poorly soluble substances in an aqueous solution. They make it possible to lower the cloud point.

The hydrotropic agent is especially selected from arylsulfonic acids and alkyl glucosides. Among the alkyl glucosides that may be used, mention may be made of heptyl glucoside, octyl glucoside or decyl glucoside. The hydrotropic agent is preferably heptyl glucoside.

"Surfactant" denotes a non-volatile compound of amphiphilic nature comprising a polar hydrophilic portion and an apolar hydrophobic portion. A surfactant lowers the surface tension of aqueous solutions and decreases the interfacial tension between water and an immiscible organic liquid. It thus makes it possible to solubilize two immiscible phases, such as water and oil, by interacting with water via its polar portion and with oil via its apolar portion. The surfactant according to the invention is selected from the four categories of surfactants:
anionic: the hydrophilic portion is negatively charged,
non-ionic: the compound does not comprise any charge, amphoteric or zwitterionic: the hydrophilic portion comprises a positive charge and a negative charge, the overall charge being zero. The zwitterionic surfactant is permanently charged, whereas the amphoteric surfactant ionizes as a function of the pH, and cationic: the hydrophilic portion is positively charged.

The amount of surfactant(s) in the microemulsions according to the invention is between 1% and 10% by weight, preferably between 1% and 5% by weight relative to the total weight of microemulsion.

Advantageously, the microemulsion of the invention contains at least one anionic surfactant, preferably selected from:

alkyl sulfonates, especially dihexyl sulfosuccinate (DHS) of formula

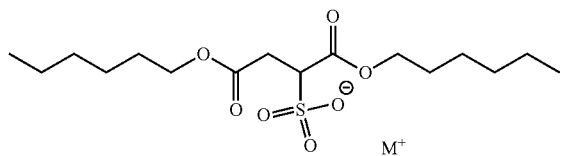

wherein
$M^+$ represents $Na^+$, $K^+$, $NH_4^+$, $(HOCH_2CH_2)_3NH^+$,
or especially the 2-ethylhexyl sulfosuccinate (Aerosol OT® or AOT, from CYTEC) of formula

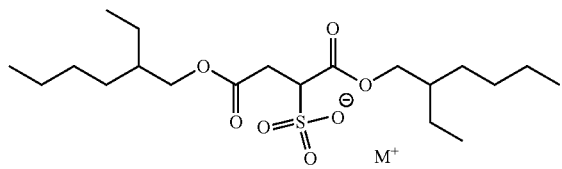

wherein
$M^+$ represents $Na^+$, $K^+$, $NH_4^+$, $(HOCH_2CH_2)_3NH^+$,
alkylaryl sulfonates of formula

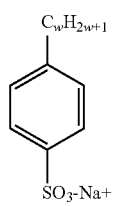

wherein w is an integer from 8 to 12,
in particular isooctyl, isononyl and especially sodium isododecylbenzenesulfonate (SDBS) of formula

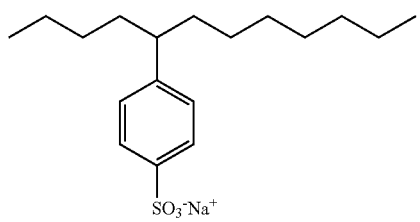

propoxysulfates, especially the Alfoterra® compounds of formula

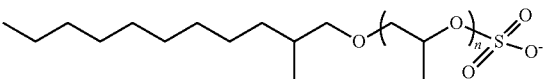

wherein the number of propoxylate units n is from 4 to 8,
n possibly being especially equal to 4 (Alfoterra® 4S, Alf4S),
n possibly being especially equal to 8 (Alfoterra® 8S, Alf8S),
alkyl sulfates, especially salts of lauryl sulfate such as sodium dodecyl sulfate (SDS) and sodium alkylether sulfates such as sodium lauryl ether (laureth) sulfate (LES),
and salts of fatty acids of formula $R-CO_2^-\ M^+$, wherein R represents a linear or branched, saturated or unsaturated carbon-based chain containing 8 to 18 carbon atoms, and $M^+$ represents a cation selected from the ions $Na^+$, $K^+$, $NH_4^+$, $(HOCH_2CH_2)_3NH^+$, especially the oleic acid salt of formula $CH_3(CH_2)_7CH=CH(CH_2)_7CO_2^-\ M^+$, wherein $M^+$ has the above-defined meanings. The microemulsion of the invention preferably comprises at least one anionic surfactant selected from sodium dodecyl sulfate and sodium laureth sulfate.

In another advantageous manner, the microemulsion of the invention contains at least one non-ionic surfactant selected from:
alkanolamides, especially the monoethanolamide (cocamide, MEA) of formula

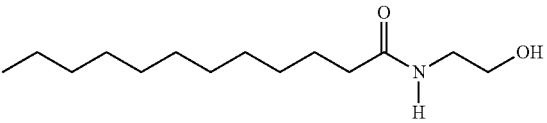 [SMILES: CCCCCCCCCCCC(=O)NCCO]

with the proviso that said alkanolamide is not a polyol,
alkylpolyglycosides (APGs),
polyglycerol ethers,
and polyglycerol esters.

In another advantageous manner, the microemulsion of the invention contains at least one amphoteric surfactant selected from:
betaines, especially cocamidopropyl betaine (CAPB) of formula

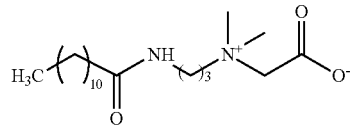

and amine oxides, especially lauryldimethylamine oxide of formula

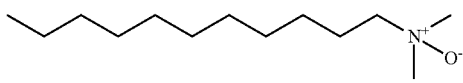

Alternatively, the microemulsion of the invention contains at least one cationic surfactant, preferably selected from:

tetraalkylammonium salts, especially dialkyldimethylammonium salts of formula $$H_3C{-}(CH_2)_n{-}\overset{\underset{\displaystyle CH_3}{|}}{\underset{\underset{\displaystyle CH_3}{|}}{N^+}}{-}(CH_2)_n{-}CH_3 \quad X^-$$

wherein $X^-$ represents an anion selected from $Cl^-$, $Br^-$, $I^-$, $CH_3COO^-$ or lactate, n is the number of methylenes, from 6 to 12, preferably a didecyldimethylammonium salt of formula $$H_3C{-}(CH_2)_9{-}\overset{\underset{\displaystyle CH_3}{|}}{\underset{\underset{\displaystyle CH_3}{|}}{\overset{\oplus}{N}}}{-}(CH_2)_9{-}CH_3 \quad X^-$$

wherein $X^-$ has the meanings given above, trialkylammonium salts, in particular trialkylammonium halides, especially dodecyltrimethylammonium bromide (DTAB) of formula $H_3C(CH_2)_{11}N^+(CH_3)_3$, pyridinium salts, especially cetylpyridinium salt of formula wherein $X^-$ has the meanings given above, benzalkonium salts, especially salts of formula wherein $X^-$ has the meanings given above, p is from 8 to 18, ammonium salts of triethanolamine of formula $(HO{-}CH_2{-}CH_2)_3NH^+X^-$ wherein $X^-$ has the meanings given above.

Highly advantageously, the microemulsions of the invention are thermodynamically stable and have a transparent or translucent appearance and, even more advantageously, the microemulsions of the invention are thermodynamically stable and have a transparent or translucent appearance for at least one or two years.

The microemulsion according to the invention preferably consists of:
- 70% to 90% of water,
- 5% to 12% of at least one hydrophobic fragrancing substance,
- 4% to 18% of at least one volatile solvo-surfactant, and
- 0.1% to 10%, preferably 1% to 5%, of at least one hydrotropic agent or at least one surfactant selected from anionic surfactants, cationic surfactants, amphoteric surfactants and non-ionic surfactants.

The microemulsions of the invention are advantageously used for the preparation of compositions applied in:
- fine fragrance, or
- cosmetics and body hygiene products.

Thus, the present invention also relates to the use of a microemulsion according to the invention, for the preparation of a fine fragrance composition, or of a cosmetic or body hygiene composition.

The microemulsions may be used in cosmetics. They may then contain one or more compounds selected from silicones, paraffin oil, isooctane, isodecane, squalene, squalane, sebum and lanolin.

In the following examples, the structures and names are as follows:

| NAMES | ABBREVIATIONS | STRUCTURES |
|---|---|---|
| SOLVO-SURFACTANTS (SS) | | |
| Isosorbide derivatives | | |
| Propylisosorbide | $C_3Iso$ | |
| Butylisosorbide | $C_4Iso$ | |
| Pentylisosorbide | $C_5Iso$ | | n = 3, 4 or 5

| NAMES | ABBREVIATIONS | STRUCTURES |
|---|---|---|
| Monomethylayed glycerol derivatives | | |
| Monomethylated propylglycerol | C301 | 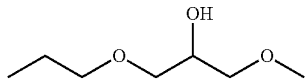 |
| | C310 | |
| Monomethylated butylglycerol | C401 | 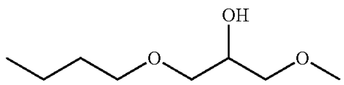 |
| | C410 | |
| Monomethylated pentylglycerol | C501 | 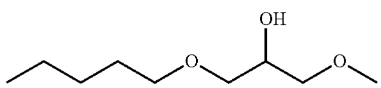 |
| | C510 | |

EXAMPLE 1: SYNTHESIS OF THE SOLVO-SURFACTANTS ACCORDING TO THE INVENTION

The syntheses of 1-methoxy-3-propoxypropan-2-ol (C301) and 1-methoxy-3-pentoxypropan-2-ol (C501) are carried out in two steps. The synthesis of 1-methoxy-3-butoxypropan-2-ol (C401) is carried out simply by opening the epoxide, insofar as the starting reagent, butylglycidol, is commercially available.

I—Synthesis of the Monomethylated Glycerol Derivatives a) Condensation of the Alcohol to Epichlorohydrin The condensation of the alcohol (1 mol) to epichlorohydrin is carried out with a slight excess of epichlorohydrin (1.5 mol) in the presence of $ZnCl_2$ as catalyst. The epichlorohydrin is added dropwise for 1 h at 100° C. The reaction medium is then kept at 115° C. for 5 h then cooled to 50° C. NaOH (2.3 moles) at 48% is then added dropwise for 1 h. All these synthesis steps are carried out with vigorous stirring. Once the reaction has ended, distilled water is added and the product is then washed twice with water to eliminate residual salts.

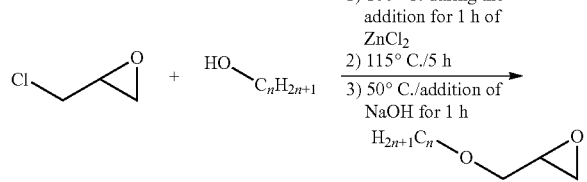

Synthesis of $C_n$glycidol, where n=3, 5

The product obtained is finally distilled under vacuum at 10-20 mbar between 75 and 80° C.

b) Opening of the Epoxide with Methanolate

The $C_n$glycidol (where n=3, 4, 5) is added dropwise to a solution of methanol containing sodium methanolate obtained beforehand by reaction between methanol and solid sodium. The addition is carried out at reflux at 80° C. for 30 min, then the temperature of 80° C. is maintained for 24 h until the $C_n$glycidol disappears entirely:

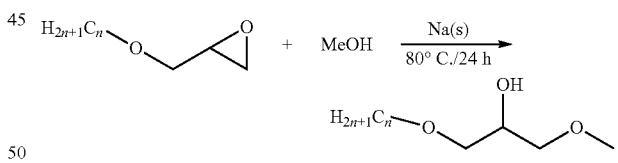

Opening of the Epoxide by Sodium Methanolate
Purification:

The methanol is evaporated on a rotary evaporator once the reaction has ended. The product obtained is then washed with two aqueous solutions saturated with NaCl: one containing 3.4% HCl and the other containing 10% $NaHCO_3$.

II—Synthesis of C3Iso, and also C4Iso and C5Iso

Isosorbide consists of two rings each having a hydroxyl function, the functions being non-equivalent at positions 2 and 5. They are referred to, respectively, as exo and endo positions. The intramolecular hydrogen bond of the hydroxyl function at position 5 and the oxygen borne by the adjacent ring differentiates the reactivities of the two positions and also the properties of the derivatives obtained.

The reactivity of the hydroxyl groups is different. It is possible to adjust the reaction parameters (solvent, base, reagents) to obtain different ratios of isosorbide derivatives (endo monoether, exo monoether and diether). The solvents and bases used to carry out the alkylation are, respectively, DMSO and KOH. This is because, with this combination, the expected endo/exo ratio will be 1/1. It is also possible to use LiOH, making it possible to predominantly obtain the exo form. The reaction is a "one pot" reaction with 1 equivalent of base, of isosorbide and of $C_n$Br bromoalkyl. First of all, the isosorbide is dissolved in the DMSO, then the mixture is heated to 90° C. KOH is then added. Once the latter dissolves entirely (1 h), the $C_n$Br is added dropwise for 1 h at reflux at 90° C. The reaction is stopped after 24 h:

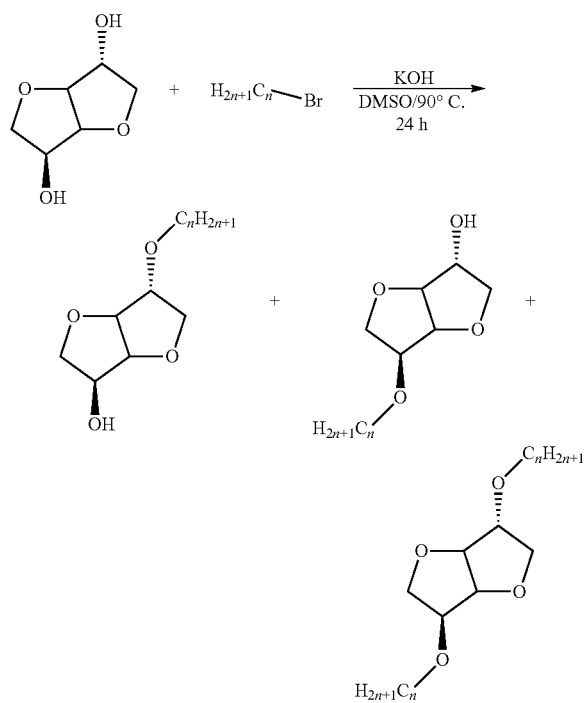

Synthesis of isosorbide monoalkyls $C_n$ Iso, where n=3, 4 or 5

Three products are obtained: two monoethers (endo and exo) and the diether.

Purification:

Once the reaction has ended, it is necessary to rebalance the pH of the solution. NaHCO$_3$ is added for this purpose. Next, in order to eliminate as much salt as possible, filtration over sintered glass is carried out with two washes with DMSO. The reaction mixture is subsequently distilled to eliminate the DMSO from the solution. The residue from the distillation is subsequently dissolved in ethyl acetate then washed twice with water saturated with NaCl. The ethyl acetate is subsequently evaporated on a rotary evaporator to recover the isosorbide derivatives present in the organic phase.

The mono- and diethers are separated using a silica column. This separation step makes it possible to obtain only the two monoethers and to eliminate the diether and the remaining isosorbide. The eluent chosen is an ethyl acetate/petroleum ether (20/80) mixture.

It is possible to separate the endo and exo isomers using separation by chromatography by solid deposition. This technique makes it possible to make the elution of the products more uniform and hence to more easily separate the two isomers. The product is firstly homogenized with the silica using dichloromethane. Once the solvent is evaporated on a rotary evaporator, the solid containing the product is placed at the top of a conventional chromatography column. The elution then proceeds conventionally with a petroleum ether/ethyl acetate (75/25) eluent. Once the first isomer has eluted, the polarity of the eluent is changed to more rapidly recover the second isomer. The eluent chosen is a 50/50 petroleum ether/ethyl acetate mixture. The two endo and exo isomers are thus obtained separately.

EXAMPLE 2: SOLUBILIZATION OF FRAGRANCE CONCENTRATES

Solubilization by Solvo-Surfactants Alone:
Solubilization of Three Fragrances and Linalool
For these reference tests, the aim of which was to classify the solvo-surfactants according to their capacity to solubilize (or not) the fragrances, the amount of fragrance was fixed at 5% by weight in milliQ water. The solubilizations of the fragrance concentrates PF1, PF2 and PF3 and also linalool were evaluated.

It appears that, in order to solubilize the fragrance concentrates or the linalool, it is necessary to have a concentration of solvo-surfactant (SS) of greater than 35%, regardless of the solvo-surfactant. From all the SSs studied, C4Iso and C3O1 appear to be the most effective for solubilizing the fragrances alone.

Solubilization by Surfactants Alone:
Secondly, the minimum amount necessary for each surfactant, used alone, to solubilize 10% of fragrance in milliQ water was determined.

The results show that CrodaSinic LS30 (sodium lauroylsarcosinate) has poor solubilizing power for the fragrance concentrates.

The best formulations for the 3 fragrance concentrates are:
11.5% DTAB (cationic surfactant) for PF2 and PF3;
18% SDS (anionic surfactant) for PF1.

In conclusion, over all the solubilization tests either with the solvo-surfactant alone or the surfactant alone, it is observed that it is necessary to have at least 35% of SS to solubilize 5% fragrance and 11-12% surfactant (SA) to solubilize 10% thereof.

Solubilization by Combining Solvo-Surfactants/Surfactants:
The combinations between the SSs, i.e. C$_3$Iso/C$_4$Iso/C3O1/C4O1/C5O1, and the SAs, i.e. SDS/LES/DTAB/DHS/CAPB, were evaluated for the solubilization of 10% of the fragrance concentrates PF1 to PF3.

Optimum Solubilization
The optimum amounts of SS and SA required to solubilize each concentrate were determined by successive additions of the two compounds until a clear phase was obtained. This gives the variation in the amount of surfactant to use in order to solubilize the three concentrates with an amount of SS fixed at 17%.

For the same concentration of SS, the amounts of SA required are significantly different depending on the fragrance concentrate to be solubilized and the SS. Generally speaking, it is observed that SDS, LES, DHS and DTAB are more effective at producing a clear formulation. The amphoteric SA CAPB gives poorer results. Moreover, for all the concentrates, the greater the number of carbons in the alkyl chain of the SS, the less SA needs to be used. This observation goes against the trend observed during the use of solvo-surfactants alone. This is due to the increase in the SS/SA interaction during solubilization.

It is thus possible to note that the amount of surfactant required for solubilization varies according to the concentrate being studied.

The optimum formulations for each concentrate are as follows:

| Fragrance concentrate | % concentrate | % SS | % SA |
|---|---|---|---|
| PF2 | 9.4 | 17.5 | 4.5 |
| PF1 | 9.9 | 17.0 | 5.2 |
| PF3 | 9.2 | 17 | 5.4 |

Each of the above formulations makes it possible to solubilize 10% of fragrances. The influence of the amount of fragrance to be solubilized on the amount of SDS required for the solubilization of the concentrate PF2 was studied in the presence of 17% C501. It is observed that the change in the % of SDS increases linearly with the amount of fragrance.

Optimization of the Solvo-Surfactant/Surfactant Ratio

Over the numerous tests carried out, it was observed that, depending on the fragrance, the amount of surfactant required depends on the amount of solvo-surfactant. We therefore conducted a slightly more systematic study so as to determine the trends and to refine this ratio which, moreover, will also depend on the stability of the formulation over a temperature range extending from 5 to 45° C. The systems studied are summarized in the following table:

| Fragrance concentrate | SS | SA |
|---|---|---|
| PF2 | $C_4$Iso | LES |
| PF2 | C501 | SDS |
| PF3 | $C_4$Iso | LES |
| PF3 | C501 | SDS |

The results obtained for each system show that the two concentrates have the same behavior depending on the solvo-surfactant—surfactant pair used. In both cases, a reduction in the amount of solvo-surfactant leads to an increase in the amount of surfactant required for solubilization. For the $C_4$Iso/LES pair, a reduction in the amount of $C_4$Iso induces an exponential increase in LES. For this pair, it is preferable to choose a formulation with a concentration of solvo-surfactant greater than 20% in order to avoid using too much surfactant. For the C501/SDS pair, a reduction in solvo-surfactant only induces a small increase in the amount of SDS. The formulations containing relatively little solvo-surfactant may thus be used to solubilize concentrates because the corresponding amounts of surfactant remain small. In conclusion, it is observed that there is no linear evolution in the ratio.

Temperature Stability of the Formulations

In order to be acceptable, the above formulations must be temperature stable over a range from ° C. to 45° C. or preferentially from 15° C. to 45° C. The formulations are therefore placed in a bath at 5° C. and at 45° C., or from 15° C. to 45° C., for 24 h. After observation, the clear formulations are considered to be stable and the cloudy formulations are considered to be unstable. Table 1 below gives the stable compositions ("OK") and the compositions that led to destabilization (appearance of cloudiness) ("KO").

TABLE 1

Stability of formulations containing 10% fragrance at 5° C. (or 15° C.), 25° C. and 45° C.

| | 5° C. | 25° C. | 45° C. |
|---|---|---|---|
| PF2: | | | |
| C3Iso: 16.5-17.2% | 8.5% SDS: OK | 8.5% SDS: OK | 8.5% SDS: OK |
| | 10% LES: OK | 10% LES: OK | 10% LES: OK |
| C4Iso: 16-17.5% | 10% LES: OK | 5.3% SDS: OK | 5.3% SDS: OK |
| | 5.3% SDS: KO | 3.1% LES: OK | 3.1% LES: OK |
| | 3.1% LES: KO | | |
| PF1: | | | |
| C3Iso: 16.5% | 11.7% SDS: OK | 11.7% SDS: OK | 11.7% SDS: OK |
| | 12.6% LES: OK | 12.6% LES: OK | 12.6% LES: OK |
| C4Iso: 16.6% | | 8.2% SDS: OK | 8.2% SDS: OK |
| | 8.2% SDS: KO | 8.6% LES: OK | 8.6% LES: KO |
| | 8.6% LES: KO | | |
| PF3: | | | |
| C3Iso: 17% | 9.2% SDS: OK | 9.2% SDS: OK | 9.2% SDS: OK |
| | 10% LES: KO | 10% LES: OK | 10% LES: OK |
| C4Iso: 17-18% | 5.1% SDS: KO | 5.1% SDS: OK | 5.1% SDS: OK |
| | 4.3% LES: KO | 4.3% LES: OK | 4.3% LES: OK |
| | 15° C. | 25° C. | 45° C. |
| PF2: | | | |
| C3O1: 16.5% | 8.4% SDS: OK | 8.4% SDS: OK | 8.4% SDS: OK |
| C4O1: 17.5% | 5.4% SDS: OK | 5.4% SDS: OK | 5.4% SDS: KO |
| C5O1: 17% | 4.6% SDS: OK | 4.6% SDS: OK | 4.6% SDS: KO |
| PF1: | | | |
| C3O1: 16.4% | 11.2% SDS: OK | 11.2% SDS: OK | 11.2% SDS: OK |
| C4O1: 17% | 7.2% SDS: OK | 7.2% SDS: OK | 7.2% SDS: OK |

TABLE 1-continued

Stability of formulations containing 10% fragrance at 5° C. (or 15° C.), 25° C. and 45° C.

PF3:

| | | | |
|---|---|---|---|
| C301: 16.5% | 8.8% SDS: OK | 8.8% SDS: OK | 8.8% SDS: OK |
| C401: 17% | 6.7% SDS: OK | 6.7% SDS: OK | 6.7% SDS: OK |
| C501: 13% | 4.7% SDS: OK | 4.7% SDS: OK | 4.7% SDS: KO |

OK = stable;
KO = not stable

Depending on the solvo-surfactant used, the stabilities at the different temperatures are not the same. The system $C_3Iso$/SDS demonstrates stability over the whole temperature range for the 3 fragrance concentrates. For the other solvo-surfactants, the formulations are not stable at all the temperatures. It should be noted that, unlike $C_4Iso$, $C_3Iso$ comprises endo and exo forms. Moreover, C401 and C501 have a cloud point, reflecting the temperature from which the solvo-surfactant is no longer water-soluble and aggregates to form a cloudy mist in the water. This cloud point may explain the instability at 45° C. of the formulations using C501 and C401. The cloud point of C501 is approximately 10° C., however the formulations remain clear at room temperature. This stability at a temperature higher than that of the cloud point of the solvo-surfactant is explained by the increase in the cloud point of C501 when SDS is added. The effect of urea, dipropylene glycol (DPG) and SDS on the cloud point of C401 and C501 was tested. The results show that it is possible to increase the cloud point of the two solvo-surfactants by adding urea and DPG. This increase nonetheless remains much smaller than that observed when SDS is added.

In light of these results, formulations containing a mixture of 2 solvo-surfactants were prepared: one giving good temperature stability and the other good solubilization effectiveness, with the aim of ascertaining whether it is thus possible to increase the temperature stability range while increasing the solubilization effectiveness. C501 was identified as having good effectiveness, and $C_3Iso$ makes it possible to obtain good temperature stability. The 2 solvo-surfactants were mixed at different ratios and for each mixture, the optimum formulation of solubilization in the presence of SDS was determined. 10% of PF2 were solubilized for each formulation.

TABLE 2

Ratio between the 2 solvo-surfactants for which transparency of the formulations is obtained

| PF2 | 5° C. | 25° C. | 45° C. |
|---|---|---|---|
| 50/50 | OK | OK | OK |
| 60/40 | OK | OK | OK |

The concentrations of SDS required to solubilize the fragrances in water are similar to those required when C501 is used alone (≈5-6%). Good temperature stability from 5 to 45° C. is obtained for several $C_3Iso$/C501 ratios.

The synergistic effect between the solvo-surfactants and the surfactants was then demonstrated by a substantial decrease in the amount of active material in the formulations based on the solvo-surfactant/surfactant systems compared to the formulations with surfactants or solvo-surfactants alone.

EXAMPLE 3: SOLUBILIZATION OF FRAGRANCE CONCENTRATES

1) Tests with C501 and C510:
The following compositions are prepared:

| Surfactant (SA) | Trade name | fragrance % (gamma-undeca-lactone) | C501% | water % | SA AM % |
|---|---|---|---|---|---|
| Sodium lauroyl sarcosinate | Crodasinic LS 30 | 4.92 | 10.38 | 78.30 | 6.40 |
| Sodium cocoyl isethionate | Hostapon SCI 85 | 4.96 | 10.57 | 78.37 | 6.10 |
| Sodium lauroyl glutamate | Hostapon CLG | 4.97 | 10.15 | 70.46 | 14.42 |
| Cocamidopropyl betaine | Genagen CAB 818 | 5.13 | 10.83 | 74.76 | 9.28 |
| Cocamidopropyl hydroxysultaine | Amonyl 675 SB | 4.99 | 10.24 | 69.96 | 14.80 |
| Heptyl glucoside (hydrotrope) | Sepiclear G7 | 5.00 | 10.63 | 73.83 | 10.54 |
| Ammonium lauryl sulfate | Texapon ALSbenz | 4.92 | 10.08 | 81.37 | 3.63 |
| Sodium cocosulfate | Texapon K30 UP | 4.90 | 9.82 | 81.05 | 4.23 |
| Sodium sulfonate C14-C17 sec alkyl | Hostapur SAS 30 | 5.00 | 9.83 | 81.61 | 3.56 |
| Sodium lauryl sulfate | / | 4.99 | 9.28 | 81.40 | 4.32 |
| Sodium lauryl sulfate | / | 5.00 | 9.13 | 81.56 | 4.31 |
| Sodium lauryl sulfate | / | 5.00 | 11.44 | 81.54 | 2.01 |

AM = Active material

It is observed that all the compositions prepared are transparent and stable.

2) Tests with C510 and Different Fragrances:
The following fragrances A, B and C are prepared:

| Fragrance A | % |
|---|---|
| Gamma-undecalactone | 20 |
| Gamma-methyl ionone | 20 |
| Beta-ionone | 20 |
| Cis-3-hexenyl acetate | 20 |
| Iso gamma super | 20 |

| Fragrance B | % |
|---|---|
| Helional | 20 |
| Triplal | 20 |
| Hexyl cinnamic aldehyde | 20 |
| Cis-3-hexenyl benzoate | 20 |
| Eugenol | 20 |

| Fragrance C | % |
|---|---|
| Helional | 20 |
| Gamma-methyl ionone | 20 |
| Beta-ionone | 20 |
| Cis-3-hexenyl acetate | 20 |
| Iso gamma super | 20 |

Then, the following compositions are prepared:

| Name of fragrance | % Fragrance | C510 % | Water % | SDS AM % |
|---|---|---|---|---|
| PA | 4.96 | 10.39 | 82.64 | 2.01 |
| PB | 4.95 | 10.03 | 79.21 | 5.81 |
| PC | 5.00 | 9.95 | 80.03 | 5.02 |

SDS AM: sodium dodecyl sulfate, active material

It is observed that all the compositions prepared are transparent and stable.

EXAMPLE 4: PERFUME FORMULATIONS

The following perfume extract (P) was prepared:

| Name of fragrance | % | CAS # |
|---|---|---|
| GAMMA-UNDECALACTONE | 0.5 | 104-67-6 |
| CIS-3-HEXENYL ACETATE | 1.0 | 3681-71-8 |
| HEXYLCINNAMIC ALDEHYDE | 12.0 | 101-86-0 |
| HEXENYL CIS-3-BENZOATE | 2.0 | 25152-85-6 |
| EUGENOL | 2.0 | 97-53-0 |
| HELIONAL | 5.0 | 1205-17-0 |
| BETA-IONONE | 3.0 | 14901-07-6 |
| GAMMA-METHYLIONONE | 5.0 | 127-51-5 |
| BENZYL PROPIONATE | 1.0 | 122-63-4 |
| TRIPLAL | 0.5 | 68039-49-6 |
| BENZYL ACETATE | 5.0 | 140-11-4 |
| HEDIONE HC | 30.0 | 24851-98-7 |
| ISO GAMMA SUPER | 26.0 | 68155-66-8 |
| CIS-3-HEXENYL SALICYLATE | 5.0 | 65405-77-8 |
| VANILLIN | 2.0 | 121-33-5 |

Then, the following formulations were prepared:

| Nature of the solvo-surfactant | Solvo-Surfactant | Fragrance | LES surfactant | Water |
|---|---|---|---|---|
| C410 | 14.5% | 5% | 5% | 72.4% |
| C401 | 20% | 5% | 2.6% | 78.5% |

By way of comparison, 17.6% of LES alone is required to solubilize 2.9% of P.

Thus, it emerges that C401 and C410, but above all C410, are good solvo-surfactants for solubilizing P, in combination with sodium lauryl ether (laureth) sulfate (LES).

| Nature of the solvo-surfactant | Solvo-Surfactant | Fragrance | LES surfactant | Water |
|---|---|---|---|---|
| C510 | 14% | 5% | 2.5% | 78.5% |
| C501 | 14.5% | 5% | 5% | 75.5% |

C501 and C510 are therefore good solvo-surfactants for solubilizing P, in combination with IC5, sodium lauryl ether (laureth) sulfate (LES).

The invention claimed is:

1. A microemulsion of oil-in-water type comprising by weight relative to the total weight of microemulsion:
   70% to 94% of water,
   1% to 15% of at least one hydrophobic fragrancing substance,
   4% to 20% of at least one volatile solvo-surfactant, and
   0.1% to 15% of at least one hydrotropic agent or at least one surfactant selected from anionic surfactants, cationic surfactants, amphoteric surfactants and non-ionic surfactants, said solvo-surfactant being selected from monoalkylated glycerol derivatives of following formula (I):

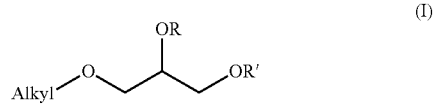

wherein the "alkyl" group is a linear or branched alkyl group comprising from 1 to 8 carbon atoms, and R and R' are each independently H or a linear or branched alkyl group comprising from 1 to 5 carbon atoms, with the proviso that R is different from R', and mixtures thereof.

2. The microemulsion as claimed in claim 1, wherein the hydrophobic fragrancing substance is a natural hydrophobic fragrancing substance selected from terpenes, essential oils and natural compounds having odoriferous properties.

3. The microemulsion as claimed in claim 1, wherein, in the monoalkylated glycerol derivative of formula (I), the "alkyl" group is a linear alkyl group comprising 3, 4 or 5 carbon atoms, and R and R' are each independently H or a methyl or ethyl group, with the proviso that R is different from R'.

4. The microemulsion as claimed in claim 1, wherein, in the monoalkylated glycerol derivative of formula (I), the "alkyl" group is a linear alkyl group comprising 3, 4 or 5 carbon atoms, and R is a methyl group, and R' is H.

5. The microemulsion as claimed in claim 1, which is free of ethanol.

6. The microemulsion as claimed in claim 1, consisting of:
   70% to 90% of water,
   5% to 12% of at least one hydrophobic fragrancing substance,
   4% to 18% of at least one volatile solvo-surfactant, and
   0.1% to 10% of at least one hydrotropic agent or at least one surfactant selected from anionic surfactants, cationic surfactants, amphoteric surfactants and non-ionic surfactants.

7. The microemulsion as claimed in claim 1, wherein the surfactant is an anionic surfactant selected from:
   alkyl sulfonates,
   alkylaryl sulfonates of formula

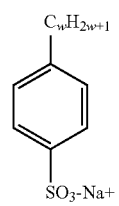

wherein w is an integer from 8 to 12, propoxy sulfates of formula

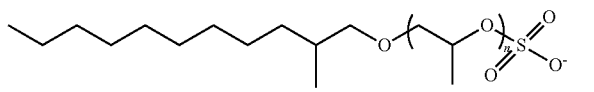

wherein the number of propoxylate units n is from 4 to 8,
alkyl sulfates,
and salts of fatty acids of formula R—$CO_2^-$ $M^+$, wherein R represents a linear or branched, saturated or unsaturated carbon-based chain containing 8 to 18 carbon atoms, and $M^+$ represents a cation selected from the ions $Na^+$, $K^+$, $NH_4^+$, $(HOCH_2CH_2)_3NH^+$.

8. The microemulsion as claimed in claim 1, wherein the surfactant is a non-ionic surfactant selected from:
alkanolamides, with the proviso that said alkanolamide is not a polyol,
alkylpolyglycosides,
polyglycerol ethers,
and polyglycerol esters,
the surfactant is an amphoteric surfactant selected from:
betaines,
and amine oxides, or
the surfactant is a cationic surfactant selected from:
tetraalkylammonium salts,
trialkylammonium salts,
pyridinium salts,
benzalkonium salts,
ammonium salts of triethanolamine of formula (HO—$CH_2$—$CH_2$)$_3$$NH^+$$X$— wherein
$X^-$ represents an anion selected from Cl—, Br—, I—, CH3COO— or lactate.

9. The microemulsion as claimed in claim 1, wherein the hydrotropic agent is selected from arylsulfonic acids and alkyl glucosides.

10. A fine fragrance composition or a cosmetic or body hygiene composition, comprising the microemulsion of claim 1.

11. The microemulsion as claimed in claim 7, wherein the anionic surfactant is selected from:
dihexyl sulfosuccinate of formula:

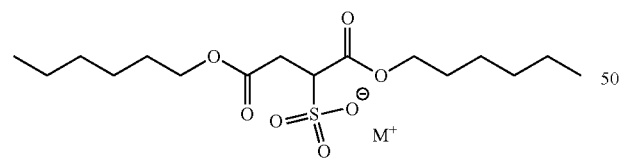

wherein $M^+$ represents $Na^+$, $K^+$, $NH_4^+$, $(HOCH_2CH_2)_3NH^+$ or 2-ethylhexyl sulfosuccinate of formula:

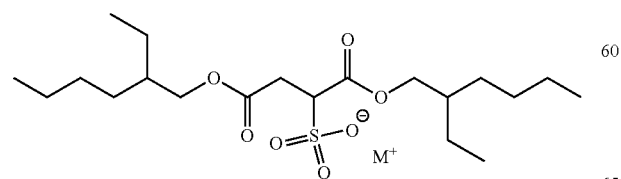

wherein $M^+$ represents $Na^+$, $K^+$, $NH_4^+$, $(HOCH_2CH_2)_3NH^+$, isododecylbenzenesulfonate of formula:

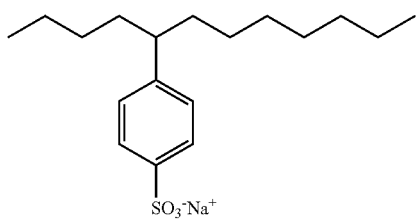

salts of lauryl sulfate chosen from sodium dodecyl sulfate and sodium alkylether sulfates,
the oleic acid salt of formula $CH_3(CH_2)_7CH$=$CH(CH_2)_7CO_2^-M^+$,
wherein $M^+$ has the meaning as defined above.

12. The microemulsion as claimed in claim 8, wherein:
the surfactant is an non-ionic surfactant selected from monoethanolamide of formula

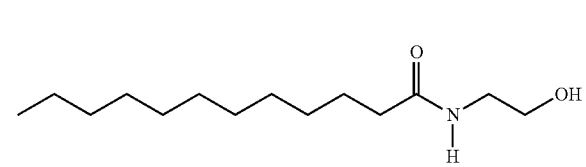 [SMILES: CCCCCCCCCCCC(=O)NCCO]

the surfactant is an amphoteric surfactant selected from:
cocamidopropyl betaine of formula

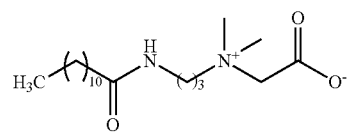

lauryldimethylamine oxide of formula

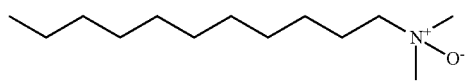

the surfactant is a cationic surfactant selected from:
dialkyldimethylammonium salts of formula

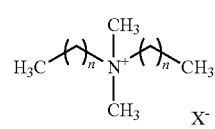

wherein
$X^-$ represents an anion selected from $Cl^-$, $Br^-$, $I^-$, $CH_3COO^-$ or lactate,
n is the number of methylenes, from 6 to 12,

23 trialkylammonium halides,
cetylpyridinium salt of formula

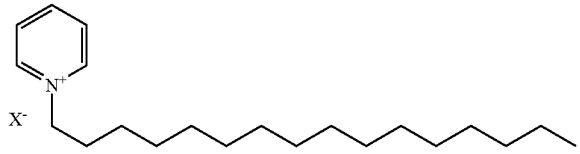

wherein X⁻ has the meanings given above,
benzalkonium salts of formula

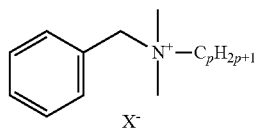

24 wherein
X⁻ has the meanings given above,
p is from 8 to 18.

13. The microemulsion as claimed in claim 12, wherein:
dialkyldimethylammonim salts are a didecyldimethylammonium salt of formula:

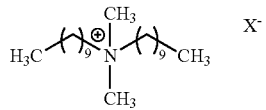

wherein X⁻ represents an anion selected from Cl⁻, Br⁻, I⁻, $CH_3COO^-$ or lactate,
trialkylammonium halides are dodecyltrimethylammonium bromide of formula $H_3C(CH_2)_{11}N^+(CH_3)_3$.

* * * * *